United States Patent [19]

Giudicelli et al.

[11] 4,017,623

[45] Apr. 12, 1977

[54] ESTERS OF 2-[(4-QUINOLYL)AMINO]-BENZOIC ACIDS IN ANALGESIC AND ANTI-INFLAMMATORY COMPOSITIONS

[75] Inventors: Don Pierre René Lucien Giudicelli, Fontenay-sous-Bois; Henry Najer, Paris; Philippe Michel Jacques Manoury, L'Hay-les-Roses; André Pierre Fernand Dumas, Bagneux, all of France

[73] Assignee: Synthelabo, Paris, France

[22] Filed: Nov. 13, 1975

[21] Appl. No.: 631,673

Related U.S. Application Data

[62] Division of Ser. No. 457,174, April 2, 1974, Pat. No. 3,935,279.

[30] Foreign Application Priority Data

| | | |
|---|---|---|
| Apr. 6, 1973 | France | 73.12505 |
| May 9, 1973 | France | 73.16635 |
| Dec. 17, 1973 | France | 73.44963 |

[52] U.S. Cl. .................. 424/250

[51] Int. Cl.[2] .................. A61K 31/495

[58] Field of Search .................. 424/250; 260/268 BQ

[56] References Cited

UNITED STATES PATENTS

| | | | |
|---|---|---|---|
| 3,632,761 | 1/1972 | Graham et al. | 260/268 BQ |
| 3,668,207 | 6/1972 | Jamas | 260/268 BQ |

FOREIGN PATENTS OR APPLICATIONS

| | | |
|---|---|---|
| 1,234,490 | 3/1971 | United Kingdom |

OTHER PUBLICATIONS

A. Allais et al., Chemical Abstracts, vol. 6T pp. 1216h–d (1966).

Carron et al., Chemical Abstracts, vol. 80, p. 47862z (1974).

*Primary Examiner*—Jerome D. Goldberg

*Attorney, Agent, or Firm*—Armstrong, Nikaido & Wegner

[57] ABSTRACT

The compounds of the formula:

NH — COOH—$CH_2$—$CH_2$—N N—$R_2$ ; N ; R[1]

in which $R_1$ is chlorine, $CF_3$, or -$SCF_3$ and $R_2$ is phenyl or phenyl substituted by one or two Cl, $CH_3$, $CF_3$, $OCF_3$ or $SCF_3$ radicals, the phenyl being substituted when $R_1$ is chlorine, and their salts, having interesting analgesic and anti-inflammatory properties.

3 Claims, No Drawings

ESTERS OF 2-[(4-QUINOLYL)AMINO]-BENZOIC ACIDS IN ANALGESIC AND ANTI-INFLAMMATORY COMPOSITIONS

CROSS REFERENCE

This application is a division of application Ser. No. 457.174 filed Apr. 2, 1974, now U.S. Pat. No. 3,935,229.

The present invention relates to esters of 2-[(4-quinolyl)amino]-benzoic acids and their addition salts with pharmaceutically tolerated acids, their preparation, and medicines containing them.

Such compounds are described in French Application 72/02,035 filed by Synthelabo on Jan. 21, 1972. They can be used as analgesic and anti-inflammatory medicines.

The present invention provides new 2-[(4-quinolyl)-amino]-benzoic acid esters which have markedly improved therapeutic properties. These compounds have the formula

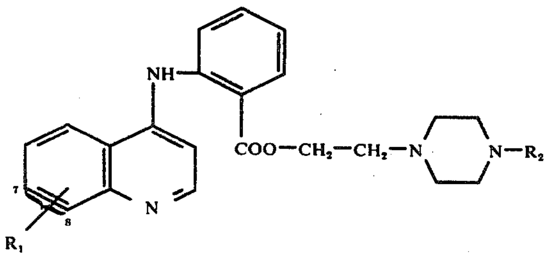

in which $R_1$ represents a chlorine atom or a $CF_3$ or $SCF_3$ group, and $R_2$ represents a phenyl radical which is unsubstituted or substituted by one or two substituents chosen from Cl, $CH_3$, $CF_3$, $OCF_3$ and $SCF_3$, provided that the phenyl radical is substituted when $R_1$ represents a chlorine atom. The invention also provides the addition salts of the compounds of formula (I) with pharmaceutically tolerated acids.

The compounds of the invention are prepared by a transesterification reaction, which may be represented by the following equation:

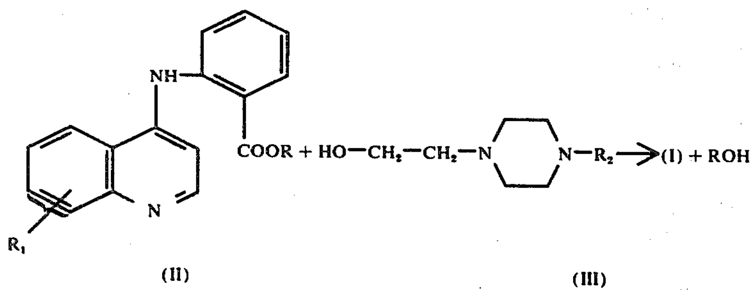

In these formulae $R_1$ and $R_2$ have the meanings given above and R represents an allyl radical or, when $R_1$ represents $SCF_3$, a methyl radical. The transesterification is advantageously carried out at the boiling point of an apolar solvent, for example, an aromatic hydrocarbon such as benzene, toluene, or xylene, in the presence of an alkali metal alcoholate and/or an alkali metal which reacts with the alcohol of the formula (III).

The compounds of the invention can also be prepared by a condensation in accordance with the following equation:

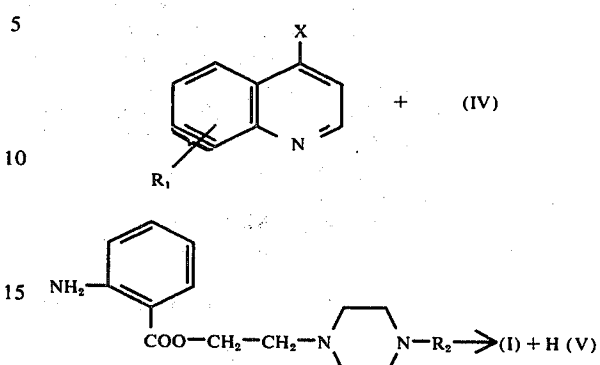

In these formulae, $R_1$ and $R_2$ have the meanings given above and X representing a halogen atom, and preferably chlorine. This condensation is advantageously carried out at the reflux temperature of a polar solvent, and in particular in an optionally acidified aqueous medium.

The following Examples illustrate the invention. The compounds of Examples 1 to 20 were prepared by the transesterification process and those of Examples 21 to 26 by the condensation process.

EXAMPLE 1

2-(4'-Phenyl-piperazino)-ethyl 2-(7'-trifluoromethyl-thio-4'-quinolyl-amino)-benzoate and its dihydro-chloride

[(I), $R_1 = SCF_3$ in the 7-position; $R_2 = C_6H_5$ Code number: SL 72 -244 ]

A mixture of 18.9 g (0.05 mol) of methyl 2-(7'-trifluoromethylthio-4'-quinolyl-amino)-benzoate, 15.95 g (0.075 mol) of 2-(4'-phenyl-piperazino)-ethanol, 0.025 g of sodium and 100 ml of anhydrous toluene is heated at the reflux temperature for 5 hours, while the methanol formed during the reaction is slowly distilled. A slight amount of insoluble matter is removed by hot filtration, and the toluene is evaporated. The residual product is dissolved in methylene chloride, the solution obtained is washed several times with water, dried over anhydrous magnesium sulphate and filtered, and the solvent is evaporated from the filtrate. The oily product obtained is dissolved in boiling isopropanol, the solution is cooled, and the precipitate is filtered off, washed with isopropyl alcohol and dried in vacuo. 20.2 g (yield = 73.1%) of 2-(4'-phenyl-piperazino)-ethyl 2-(7'-trifluoromethylthio-4'-quinolyl-amino)-benzoate are collected; m.p. 120° C.

Analysis: $C_{29}H_{27}F_3N_4O_2S$ (M.W. = 552.62)

Base determination: Equivalent, calculated : 276.3 found: 281.9.

Its dihydrochloride is prepared by adding 40 ml. (0.04 mol) of N hydrochloric acid to a solution of 11.05 g. (0.02 mol) of base in 70 ml. of methylene chloride. The salt which has separated out is filtered off, washed with water, dried and recrystallised from 250 ml. of ethanol. 9.5 g. (yield = 76%) of light yellow 2-(4'-phenylpiperazino)-ethyl 2-(7'-trifluoromethylthio-4'-quinolylamino)-benzoate dihydrochloride, m.p. 230°–232° C., are collected.

Analysis: $C_{29}H_{29}Cl_2F_3N_4O_2S$ (M.W. = 625.54

Calculated %: C 55.68, H 4.67, N 8.96, F 9.11 Ionised Cl 11.33

Found %: 55.50 4.47 8.85 9.15 11.32 55.40 4.50 8.80 9.13.

EXAMPLE 2

2-(4'-m-Trifluoromethylphenyl-piperazino)-ethyl 2-(7'-chloro-4'-quinolyl-amino)-benzoate and its dihydrochloride.

[(I); $R_1$ = Cl in the 7-position;

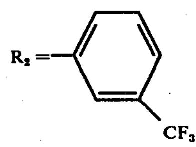

code number: SL 72 -391 ].

A mixture of 17.3 g. (0.051 mol) of allyl 2-(7'-chloro-4'-quinolyl-amino)-benzoate, 13.7 g. (0.05 mol) of 2-(4'-m-trifluoromethylphenyl-piperazino)-ethanol, 100 ml. of anhydrous toluene and 0.03 g. of ethanol, 100 ml. of anhydrous toluene and 0.03 g. of sodium is heated at the reflux temperature, while the alcohol formed during the reaction is slowly distilled off. Heating is continued until the starting ester has disappeared completely (as verified by thin layer chromatography), if necessary adding a little toluene to compensate for that which is entrained during the distillation. After the end of the reaction, the solvent is evaporated and the residue is taken up in isopropyl alcohol. The solution crystallises on cooling. The crystals are filtered off and dried, and 22.5 g. (yield = 80%) of 2-(4'-m-trifluoromethylphenyl-piperazino)-ethyl 2-(7'-chloro-4'-quinolylamino)-benzoate are finally collected, m.p. 100°–102° C.

Analysis: $C_{29}H_{26}ClF_3N_4O_2$ (M.W. = 555)

Calculated %: Cl 6.39

Found %: 6.10 .

The dihydrochloride is prepared by adding 16 ml. of a 5N solution of hydrochloric acid in ethanol to a solution of 22.20 g. (0.04 mol) of the base in 200 ml. of methylene chloride. After the solvents have been evaporated, the residue is crystallised from 250 ml. of isopropanol in 21.95 g. (yield = 87.4%) of 2-(4'-m-trifluoromethylphenyl-piperazino)-ethyl 2-(7'-chloro-4'-quinolyl-amino)-benzoate dihydrochloride, m.p. 217° C., are collected Analysis: $C_{29}H_{28}Cl_3F_3N_4O_2$ (M.W. = 627.93)

Calculated % (anhydrous): C 55.47, H 4.49, N 8.82, F 9.08. (Taking into account the 1.1% water content measured by a Karl Fischer determination):

| | | | | |
|---|---|---|---|---|
| Found : | 54.48<br>54.76<br>54.99 | 4.56<br>4.68<br>4.63 | 8.32<br>8.47<br>8.68 | 8.99<br>9.20<br>9.05 |

EXAMPLE 3

2-[4'-(2'', 3''-Dimethyl-phenyl)-piperazino]-ethyl 2-(7'-chloro-4'-quinolyl-amino)-benzoate and its dihydrochloride.

[(I); $R_1$ = Cl in the 7-position;

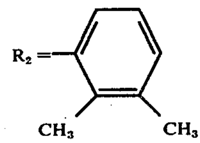

Code number: SL 72 -248 ].

Following the procedure of Example 2, but starting from 16.9 g. (0.05 mol) of allyl 2-(7'-chloro-4'-quinolyl-amino)-benzoate and 14 g. (0.06 mol) of 2-[4'-(2'', 3''-dimethylphenyl)-piperazino]-ethanol, 22.6 g. (yield = 87.9%) of 2-[4'-(2'', 3''-dimethyl-phenyl)-piperazino]-ethyl 2-(7'-chloro-4'-quinolyl-amino)-benzoate are obtained, m.p. 126° C.

Analysis: $C_{30}H_{31}ClN_4O_2$ (M.W. 32 515.06)

Calculated %: Cl 6.89

Found %: 6.87

2-[4'-(2'', 3''-Dimethyl-phenyl)-piperazino]-ethyl 2-(7'-chloro-4'-quinolyl-amino)-benzoate dihydrochloride, prepared like the dihydrochloride of Example 2, melts at 220° C.

Analysis: $C_{30}H_{33}Cl_3N_4O_2$ (M.W. = 587.98)

Calculated %: C 61.28, H 5.66, N 9.53, Ionised Cl 12.06

Found %: 61.15 5.75 9.46 12.03 61.18 5.73 9.40.

EXAMPLE 4

2-(4'-p-Chlorophenyl-piperazino)-ethyl 2-(7'-chloro-4'-quinolyl-amino)-benzoate and its dihydrochloride

[(I); $R_1$ = Cl in the 7-position;

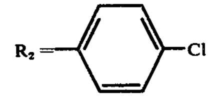

Code number: RC 72 -165 ].

By following the procedure of Example 2 and reacting 16.9 g. (0.05 mol) of allyl 2-(7'-chloro-4'-quinolyl-amino)-benzoate and 24 g. (0.1 mol) of 2-(4'-p-chlorophenyl-piperazino)-ethanol, 2-(4'-p-chlorophenyl-piperazino)-ethyl 2-(7'-chloro-4'-quinolylamino)-benzoate is prepared in a 60% yield, m.p. 145° C.

Analysis: $C_{28}H_{26}Cl_2N_2O_4$ (M.W. = 521.45)

Calculated %: Cl 13.61

Found %: 13.55.

2-(4'-p-Chlorophenyl-piperazino)-ethyl 2-(7'-chloro-4'-quinolyl-amino)-benzoate dihydrochloride, prepared in an identical manner to the dihydrochloride of Example 2, melts at 240° C.

Analysis: $C_{28}H_{28}Cl_4N_4O_2$ (M.W. = 594.37)
Calculated %: C 56.48, H 4.75, N 9.42, Cl 23.85
Found %: 56.45 4.60 9.39 23.60.

EXAMPLE 5

2-(4'-Phenyl-piperazino)-ethyl 2-(7'-trifluoro-methyl-4'quinolyl-amino)-benzoate and its dihydrochloride.

(I); $R_1 = CF_3$ in the 7-position; $R_2 = C_6H_5$ Code number: SL 72 -242 ].

A mixture of 18.6 g. (0.05 mol) of allyl 2-(7'-trifluoromethyl-4'-quinolyl-amino)-benzoate, 14.4 g. (0.07 mol) of 2-(4'-phenyl-piperazino)-ethanol, 100 ml. of anhydrous toluene and 0.02 g. of sodium is heated for five hours at the reflux temperature, while the alcohol formed during the reaction is distilled off. The solution is allowed to cool, a slight amount of insoluble matter is filtered off, the toluene is evaporated from the filtrate, and the residue is dissolved in diethyl ether. The other solution is washed several times with water, dried over magnesium sulphate and filtered, the solvent is evaporated from the filtrate, and the remainly oily product is dissolved in 200 ml. of boiling isopropyl alcohol. The solution is chilled, the precipitate is filtered off, and 20.1 g. (yield = 79%) of 2-(4'-phenylpiperazino)-ethyl 2-(7'-trifluoromethyl-4'-quinolyl-amino)-benzoate, m.p. 130° C., are finally collected.

Analysis: $C_{29}H_{27}F_3N_4O_2$ (M.W. = 520.56)
Base determination: Equivalent, calculated 260.2
Found 257.

The dihydrochloride is prepared by adding 40 ml. of an N solution of hydrochloric acid (0.04 mol) to 10.4 g. (0.02 mol) of base dissolved in 50 ml. of methylene chloride. The precipitate is filtered off, dried and recrystallised from 120 ml. of ethanol. 9.2 g. (yield = 78%) of 2-(4'-phenyl-piperazino)-ethyl 2-(7'-trifluoromethyl-4'-quinolyl-amino)-benzoate dihydrochloride are obtained, m.p. 210° C.

Analysis: $C_{29}H_{29}Cl_2F_3N_4O_2$ (M.W. = 593.48)
Calculated % (anhydrous) C 58.69, H 4.83, N 9.44, F 9.60 (Taking into account the 0.7% water content measured by a
Karl Fischer determination):

| | | | | |
|---|---|---|---|---|
| | 58.27 | 4.97 | 9.37 | 9.53 |
| Found % : | 58.17 | 5.01 | 9.36 | 9.50. |

EXAMPLE 6

2-(4'-m-Trifluoromethylphenyl-piperazino)-ethyl 2-(4'-trifluoromethyl-4'-quinolyl-amino)-benzoate and its dihydrochloride.

[(I); $R_1 = CF_3$ in the 7-position,

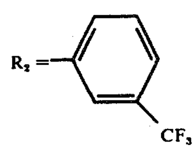

Code number: SL 73.017].

A mixture of 18.65 g. (0.05 mol) of allyl 2-(7'-trifluoromethyl-4'-quinolyl-amino)-benzoate, 16.2 g. (0.059 mol) of 2-(4'-m-trifluoromethylphenyl-piperazino)-ethanol, 150 ml. of anhydrous toluene and 0.03 g. of sodium is heated under reflux for two and a half hours, while the allyl alcohol formed during the reaction is slowly removed by distillation. A slight amount of insoluble matter is filtered off and the toluene is evaporated from the filtrate. The residue is dissolved in a mixture of methylene chloride an acetone (8:2) and this solution is passed through a silica column. Elution is carried out with the same mixture of solvents and the eluate is collected in 50 ml. fractions. These fractions are examined by thin layer chromatography. Those which contain into desired almost pure ester are combined and the solvent is driven off from them. The residual product is triturated in a mixture of ether and petroleum ether, filtered off and dried. 16.8 g. (yield 32 57%) of 2-(4'-m-trifluoromethylphenyl)-piperazino)-ethyl 2-(7'-trifluoromethyl-4'-quinolyl-amino)-benzoate, m.p. 88°–90° C., are thus isolated.

Analysis: $C_{30}H_{26}F_6N_4O_2$ (M.W. = 588.557)
Base determination: Equivalent calculated 294.2 found 298.
(Code number of the base: SL 73.033).

The dihydrochloride is prepared by dissolving 15.3 g. (0.026 mol) of the above base in 75 ml. of methylene chloride and adding 13 ml. of a 4N aqueous solution of hydrochloric acid. The salt which has precipitated is filtered off and recrystallised from isopropyl alcohol. 16.15 g. (yield = 94%) of 2-(4'-m-trifluoromethylphenyl-piperazino)-ethyl 2-(7'-trifluoromethyl-4'-quinolyl-amino)-benzoate dihydrochloride, m.p. 230° C., are thus collected.

Analysis: $C_{30}H_{28}Cl_2F_6N_4O_2$ (M.W. = 661.5)
Calculated %: C 54.47, H 4.27, N 8.47, Cl 10.72
Found %: 54.58 4.21 8.44 10.75.

EXAMPLE 7

2-(4'-m-Chlorophenyl-piperazino)-ethyl 2-(7'-chloro-4'-quinolyl-amino)-benzoate and its dihydrochloride.

[(I); $R_1 = Cl$ in the 7-position,

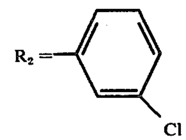

Code number: SL 73-018].

16.9 g. (0.05 mol) of allyl 2-(7'-chloro-4'-quinolyl-amino)-benzoate and 12.7 g. (0.0527 mol) of 2-(4'-m-chloro-phenyl-piperazino)-ethanol and 150 ml. of anhydrous toluene are introduced into a 250 ml. distillation flask equipped with a magnetic stirrer. A few drops of toluene are distilled off to entrain any traces of moisture, and 0.03 g. of sodium are added. A slow distillation is then effected for three hours to remove the allyl alcohol as it is formed. Insoluble matter is removed by hot filtration, the toluene is vaporated from filtrate, and the residue is recrystallised from isopropyl alcohol. 22.85 g. (yield = 33%) of 2-(4'-m-chlorophenyl-piperazino)-ethyl 2-(7'-chloro-4'-quinolyl-amino)-benzoate, m.p. 122° C., are collected.

Analysis: $C_{28}H_{26}Cl_2N_4O_2$ (M.W. = 521.4)
Base determination: Equivalent, calculated 521.4 found 522.

The dihydrochloride is prepared by dissolving 13.035 g. (0.025 mol) of base in 60 ml. of methylene chloride and adding 12.5 ml. of 4N hydrochloric acid thereto. The dihydrochloride which has precipitated is filtered off, washed with methylene chloride, dried in vacuo at 60° C., and recrystallised from alcohol. It melts at 216° C.

Analysis: $C_{28}H_{28}Cl_4N_4O_2$ (M.W. = 594.37)

| | | |
|---|---|---|
| Calculated %: | C 56.58, H. | 4.75, O 5.38, N 9.43 |
| | total | ionised |
| | Cl 23.86 | Cl 11.93 |
| Found %: | C 56.68, H | 4.89, O 5.50, N 9.47 |
| | total | ionised |
| | Cl 23.75 | Cl 11.95 |

EXAMPLE 8

2-(4'-m-Trifluoromethoxyphenyl-piperazino)-ethyl 2-(7'-chloro-4'-quinolyl-amino)-benzoate and its dihydrochloride.

[(I); $R_1$ = Cl in the 7-position,

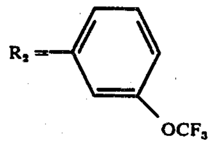

Code number: SL 73.030].

A mixture of 16.9 g. (0.05 mol) of allyl 2-(7'-chloro-4'-quinolyl-amino)-benzoate, 15.5 g. (0.0535 mol) of 2-(4'-m-trifluoromethoxyphenyl-piperazino)-ethanol, 0.03 g. of sodium and 100 ml. of anhydrous toluene is heated at the reflux temperature for two and a half hours, following the procedure of the proceeding Examples. After cooling, a slight amount of insoluble matter is filtered off and the toluene is evaporated from the filtrate. The residue is taken up in an 8:2 mixture of methylene chloride and acetone and this solution is chromatographed on a silica column. The fractions containing the desired ester are combined and the solvents are driven off. 26.6 g. of oily aminoester are thus obtained.

The dihydrochloride is prepared therefrom by dissolving the aminoester base in methylene chloride and adding the calculated amount of 4N hydrochloric acid solution in ethanol. Since the salt remains in solution, the solution is evaporated to dryness and the residue is crystallised from isopropyl alcohol. 24 g. (yield: 74.5%) of 2-(4'-m-trifluoromethoxyphenyl-piperazino)-ethyl 2-(7'-chloro-4'-quinolyl-amino)-benzoate dihydrochloride, m.p. approximately 228° C., are obtained.

Analysis: $C_{29}H_{28}Cl_3F_3N_4O_3$ (M.W. = 643.93)
Calculated %: C 54.09, H 4.38, N 8.70, Cl 11.01
Found %: 53.99 4.41 8.75 10.92.

EXAMPLE 9

2-(4'-m-Trifluoromethylthiophenyl-piperazino)-ethyl 2-(7'-chloro-4'-quinolyl-amino)-benzoate and its dihydrochloride.

[(I); $R_1$ = Cl in the 7-position;

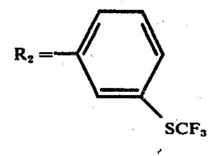

Code number: SL 73 -031 ].

By following the procedure of the preceding Examples but using 22.36 g. (0.066 mol) of allyl 2-(7'-chloro-4'-quinolyl-amino)-benzoate, 21 g. (0.0685 mol) of 2-(4'-m-trifluoromethylthiophenyl-piperazino)-ethanol, 34 g. of basic aminoester are obtained after chromatography on a silica column and evaporation to dryness of the functions containing the desired ester. The base is converted into its dihydrochloride by adding the calculated amount of hydrochloric acid in ethanol to a solution of the base in methylene chloride. After evaporation of the solvents and recrystallisation of the product from isopropyl alcohol, 32 g. (yield = 73.6%) of 2-(4'-m-trifluoromethylthiophenyl-piperazino)-ethyl 2-(7'-chloro-4'-quinolyl-amino)-benzoate dihydrochloride, m.p. 230° C., are collected.

Analysis: $C_{29}H_{28}Cl_3F_3N_4O_2S$ (M.W. = 659.99)
Calculated %: C 52.77; H 4.27, N 8.48, $Cl^-$10.74
Found %: 52.70 4.27 8.39 10.66

EXAMPLE 10

2-(4'-m-Chlorophenyl-piperazino)-ethyl 2-(7'-trifluoromethyl-4'-quinolyl-amino)-benzoate and its dihydrochloride.

[(I); $R_1$ = $CF_3$ in the 7-position,

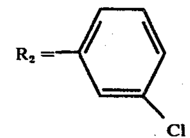

Code number: SL 73 -045 ].

By reacting a mixture of 11.2 g. (0.0465 mol) of 2-(4'-m-chlorophenyl-piperazino)-ethanol and 15.58 g. (0.0419 mol) of allyl 2-(7'-trifluoromethyl-4'-quinolyl-amino)-benzoate in toluene, and by following the procedure of the proceding Examples, a solid is obtained after removing the solvent, and this solid is recrystallised from isopropyl alcohol. 13.2 g. (yield = 65%) of 2-(4'-m-chlorophenyl-piperazino)-ethyl 2-(7'-trifluoromethyl-4'-quinolyl-amino)-benzoate, m.p. 125° C., are thus collected.

Analysis: $C_{29}H_{26}ClF_3N_4O_2$ (M.W. = 555)
Calculated %: C 62.76, H 4.72, N 10.09
Found %: 62.84 4.67 9.88.

The dihydrochloride is prepared by dissolving the above base in methylene chloride, and adding the calculated amount of a 4N solution of hydrochloric acid in ethanol. The solvents are evaporated and the dihydrochloride is recrystallised from isopropanol. 2-(4'-m-Chlorophenyl-piperazino)-ethyl 2-(7'-trifluoromethyl-4'-quinolyl-amino)-benzoate dihydrochloride melts with decomposition at 240° C.

Analysis: $C_{29}H_{28}Cl_3F_3N_4O_2$ (M.W. = 627.9)

| | | |
|---|---|---|
| Calculated % : | C 55.47, H ionised Cl 11.31 | 4.49, N 8.92 total Cl 16.94 F 9.08 |
| Found % : | C 55.54, H ionised Cl 11.35 | 4.72 N 8.79 total Cl 17.07 F 9.04. |

EXAMPLE 11

2-[4'-(3''-Chloro-2''-methyl-phenyl)-piperazino]-ethyl 2-(7'-chloro-4'-quinolyl-amino)-benzoate and its dihydrochloride.

[(I); $R_1$ = Cl in the 7-positon,

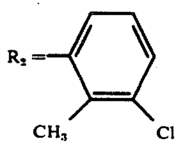

Code number: SL 73 -046 ].

Using the procedure of the preceding Examples, 9.5 g. (0.0373 mol) of 2-[4'-(3''-chloro-2''-methyl-phenyl)-piperazino]-ethanol and 11.8 g. (0.035 mole) of allyl 2-(7'-chloro-4'-quinolyl-amino)-benzoate are reacted in toluene. The solvent is evaporated and the oily residue is triturated in petroleum ether until solidification takes place. The product is filtered off, dried in air and recrystallised from isopropyl alcohol. 15.15 g. (yield = 81%) of 2-[4'-(3''-chloro-2''-methyl-phenyl)-piperazino]-ethyl 2-(7'4'-quinolyl-amino)-benzoate, m.p. 122° C., are thus collected Analysis: $C_{29}H_{28}Cl_2N_4O_2$ (M.W. = 535.38)

Calculated %: C 65.06, H 5.27, N 10.46

Found %: 65.00 5.29 10.44.

The dihydrochloride is prepared by dissolving the above base in methylene chloride and adding a calculated amount of 4N hydrochloric acid in ethanol. The solvents are evaporated and the dihydrochloride is recrystallised from isopropyl alcohol. The 2-[4'-(3''-chloro-2''-methyl-phenyl)-piperazino]-ethyl 2-(7'-chloro-4'-quinolyl-amino)-benzoate dihydrochloride obtained melts with decomposition at 210° C.

Analysis: $C_{29}H_{30}Cl_4N_4O_2$ (M.W. = 608.3) total

Calculated %: C 56.34, H 5.07, O 6.58, N 9.06 Cl 22.95

Found %: 56.50 4.96 6.49 9.18 22.79.

Calculated by taking into account a 1.5% water content measured by the Karl Fischer method.

EXAMPLE 12

2-[4'-(3''-chloro-2''-methyl-phenyl)-piperazino]-ethyl 2-(7'-trifluoromethyl-4'-quinolyl-amino)-bezoate and its dihydrochloride.

[(I); $R_1$ = $CF_3$ in the 7-position;

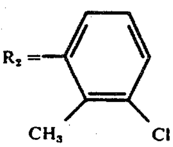

Code number: SL 73 -047 ].

A mixture of 5.4 g. (0.021 mol) of 2-[4'-(3''-chloro-2''-methyl-phenyl)-piperazino]-ethanol and 7.5 g. (0.02 mol) of allyl 2-(7'-trifluoromethyl-4'-quinolyl-amino)-benzoate is reacted in toluene, following the procedure of the preceding Examples. The toluene is evaporated and the residue is crystallised from petroleum ether. The crystals are filtered off, dried in air and recrystallised from isopropyl alcohol. 10.5 g. (yield = 92%) of 2-[4'-(3''-chloro-2''-methyl-phenyl)-piperazino]-ethyl 2-(7'-trifluoromethyl-4''-quinolyl-amino)-benzoate, m.p. 130° C., are thus obtained.

Analysis: $C_{30}H_{28}ClF_3N_4O_2$ (M.W. = 569.03) Calculated %: C 62.32, H 4.96, N 9.85

Found %: 63.36 5.14 9.84.

The dihydrochloride is prepared by dissolving the base in methyl chloride and adding a calculated amount of a 4N solution of hydrochloric acid in ethanol. The dihydrochloride is filtered off and recrystallised from isopropyl alcohol. 2-[4'-(3''-methyl-phenyl)-piperazino]-ethyl 2-(7'-trifluoromethyl-4'-quinolyl-amino)-benzoate dihydrochloride, m.p. 230° C., with decomposition is thus obtained.

Analysis: $C_{30}H_{30}Cl_3F_3N_4O_2$ (M.W. = 641.95)

Calculated %: C 56.04, H 4.88, N 8.72

Found %: 55.36 4.73 8.50

Calculated taking into account a 0.15% water content measured by the Karl Fischer method.

EXAMPLE 13

2-(4'-m-Trifluoromethylthiophenyl-piperazino)-ethyl 2-(7'-trifluoromethyl-4'-quinolyl-amino)-benzoate and its dihydrochloride.

[(I); $R_1$ = $CF_3$ in the 7-position;

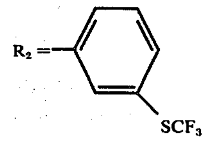

Code number: SL 73 -048 ].

By reacting 12 g. (0.039mol) of 2-(4'-m-trifluoromethylthiophenyl-piperazino)-ethanol and 13.9 g. (0.037 mol) of allyl 2-(7'-trifluoromethyl-4'-quinolylamino)-benzoate in toluene, following the technique of the preceding Examples, an oil is obtained after evaporation of the solvent, and this oil is chromatographed on a silica column and eluted with a 4:1 mixture of chloroform and actone. 20 g. (yield = 86%) of 2-(4'-m-trifluoromethylthiophenyl-piperazino)-ethyl 2-(7'-trifluoromethyl-4'-quinolyl-amino)-benzoate are thus obtained as a pale yellow oil.

Analysis: $C_{30}H_{26}F_6N_4O_2S$ (M.W. = 620.62)

Calculated %: C 58.06, H 4.22; N 9.03

Found %: 57.98 4.27 8.95.

The dihydrochloride is prepared by dissolving the oily base in methylene chloride and adding a calculated amount of a 4N solution of hydrochloric acid in ethanol. The solvents are vaporated and the residue is recrystallised from isopropyl alcohol. 2-(4'-m-Trifluoromethylthio-phenyl-piperazino)-ethyl 2-(7'-trifluoromethyl-4'-quinolylamino)-benzoate dihydrochloride, m.p. 220° C., with decomposition is thus obtained.

Analysis: $C_{30}H_{28}Cl_2F_6N_4O_2S$ (M.W. = 693.54)

Calculated %: C 51.95, H 4.07, Cl 10.22
Found %: 51.94 4.00 10.14.

EXAMPLE 14

2-(4'-, -Trifluoromethoxyphenyl-piperazino)-ethyl 2-(7'-trifluoromethyl-4'-quinolyl-amino)-benzoate and its dihydrochloride.

[(I); $R_1 = CF_3$ in the 7-position;

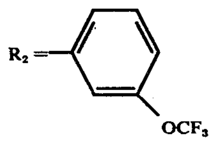

Code number: SL 73 -051 ].

10.12 g. (0.035 mol) of 2-(4'-m-trifluoromethoxy-phenyl-piperazino)-ethanol and 12.4 g. (0.0333 mol) of allyl 2-(7'-trifluoromethyl-4'-quinolyl-amino)-benzoate are reacted in toluene, following the procedure of the preceding Examples. The toluene is evaporated and the oil obtained is purified by chromatography on a silica column, eluting with a 9:1 mixture of chloroform and acetone. The solvent is evaporated and 16.5 g. (yield = 95%) of 2-(4'-m-trifluoromethoxyphenyl-piperazino)-ethyl 2-(7'-trifluoromethyl-4'-quinolyl-amino)-benzoate are obtained as an oil which cannot be crystallised.

Analysis: $C_{30}H_{26}F_6N_4O_3$ (M.W. = 604.56)
Calculated %: C 59.60, H 4.33, N 9.27
Found %: 59.35 4.26 9.10

The dihydrochloride is prepared by dissolving the above base in methylene chloride and adding a calculated amount of a 4N solution of hydrochloric acid in ethanol. The solvents are evaporated, the residue is riturated in diethyl ether and the 2-(4'-m-trifluoromethoxyphenyl-piperazino)-ethyl 2-(7'-trifluoromethyl-4'-quinolyl-amino)-benzoate dihydrochloride obtained is recrystallised from isopropyl alcohol. It then melts at 270°–272° C., with decomposition.

Analysis: $C_{30}H_{28}Cl_2F_6N_4O_3$ (M.W. = ]677.48) Calculated %: C 53.19, H 4. 17, N 8.27, F 16.82, Cl 10.47 Found %: 53.17 4.11 8.13 16.69 10.52.

EXAMPLE 15

2-(4'-m-Trifluoromethylthiophenyl-(piperazino)-ethyl 2-(7'-trifluoromethylthio-4'-quinolyl-amino)-benzoate and its dihydrochloride.

[(I); $R_1 = SCF_3$ in the 7-position;

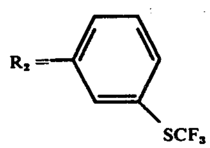

Code number: SL 73-069].

Using the procedure of the preceding Examples, a mixture of 11.35 g. (0.03 mol) of methyl 2-(7'-trifluoromethyl-thio-4'-quinolyl-amino)-benzoate, 9.8 g. (0.032 mol) of 2-(4'-m-trifluoromethylthiophenyl-piperazino)-ethanol, 150 ml. of toluene and 0.03 g. of sodium is heated for three hours. The oil is purified by chromatography on a silica column and the pure oily base obtained is crystallised by trituration in petroleum ether. 15.9 g. (yield = 81%) of 2-(4'-m-trifluoromethylthio-phenyl-piperazino)-ethyl 2-(7'-trifluoromethylthio-4'-quinolyl-amino)-benzoate are thus obtained. After recrystallisation from isopropyl alcohol, it melts and 90° C.

Analysis: $C_{30}H_{26}F_6N_4O_2S_4$ (M.W. = 652.69) Calculated %: C 55.20, H. 4.01, N 8.58 Found %: 54.62 4.00 8.46.

2-(4'-m-Trifluoromethylthiophenyl-piperazino)-ethyl 2-(7'-trifluoromethylthio-4'-quinolyl-amino)-benzoate dihydrochloride, prepared as in the preceding Examples, melts at 220° C., after recrystallisation from ethyl alcohol.

Analysis: $C_{30}H_{28}Cl_2F_6N_4O_2S_2$ (M.W. = 725.61) Calculated %: C 49.60, H 3.89, N 7.72, Cl 9.77 Found %: 49.58 3.85 7.59 9.81

EXAMPLE 16

2-[4'-(3",5"-Di-trifluoromethyl-phenyl)-piperazino]-ethyl 2-(7'-trifluoromethyl-4'-quinolyl-amino)-benzoate and its dihydrochloride.

[(I); $R_1 = CF_3$ in the 7-position;

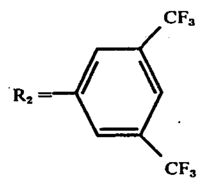

Code number: SL 73-070].

By heating 11.17 g. (0.03 mol) of allyl 2-(7'-trifluoromethyl-4'-quinolyl-amino)-benzoate, 11.3 g. (0.33 mol) of 2-[4'-(3",5"-di-trifluoromethyl-phenyl)-piperazino]-ethanol, 150 ml. of toluene and 0.03 g. of sodium for two hours thirty minutes, 16.7 g. (yield = 85%) of 2[4'-(3",5"-di-trifluoromethyl-phenyl)-piperazino]-ethyl 2-(7'-trifluoromethyl-4'-quinolyl-amino)-benzoate are obtained after the usual treatment, and this product, after recrystallisation from isopropyl alcohol, melts at 114° C.

Analysis: $C_{31}H_{25}F_9N_4O_2$ (M.W. = 656.58) Calculated %: C 56.71, H 3.83, N 8.53 Found %: 56.76 3.93 8.67

2-[4'-(3",5"-Di-trifluoromethyl-phenyl)-piperazino]-ethyl 2-(7'-trifluoromethyl-4'-quinolyl-amino)-benzoate dihydrochloride, prepared as in the preceding Examples, melts at 238° C., after recrystallisation from ethyl alcohol.

Analysis: $C_{31}H_{27}Cl_2F_9N_4O_2$ (M.W. = 729.48) Calculated %: C 51.04, H 3.73, N 7.68 Found %: 51.08 3.70 7.64.

EXAMPLE 17

2-(4'-m-Trifluoromethylphenyl-piperazino)-ethyl 2-(8'-trifluoromethyl-4'-quinolyl-amino)-benzoate.

($R_1 = CF_3$ in the 8-position;

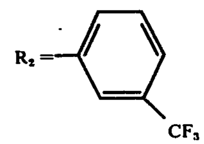

Code number: SL B 179).

10.76 g. (0.0289 mol) of allyl 2-(8'-trifluoromethyl-4'-quinolyl-amino)-benzoate, 8.23 g. (0.03 mol) of 2-(4'-m-trifluoromethylphenyl-piperazino)-ethanol and 150 ml. of anhydrous toluene are introduced into a distillation apparatus. The mixture is heated at the reflux temperature, and approximately 10 ml. of toluene are slowly distilled in order to entrain traces of water present in the reaction mixture. 0.06 g. of sodium is then added and the whole is heated for 3 hours with continuous slow distillation to remove the allyl alcohol formed during the trans-esterification reaction. The disappearance of the starting ester is checked by thin layer chromatography. The boiling reaction mixture is filtered to remove a slight amount of insoluble matter and the toluene is evaporated from the filtrate. A gummy residue is obtained and is triturated in petroleum ether. The precipitate which separates out is filtered off, washed with petroleum ether, dried in vacuo and recrystallised from isopropyl alcohol. 13.8 g. (yield = 81%) of 2-(4'-m-trifluoromethylphenyl-piperazino)-ethyl 2-(8'-trifluoromethyl-4'-quinolyl-amino)-benzoate, m.p. 114° C., are obtained.

Analysis: $C_{30}H_{26}F_6N_4O_2$ (M.W. = 588.557) Calculated %: C 61.22, H 4.45, N, 9.52 Found %: 61.01 4.72 9.40.

EXAMPLE 18

2-(4'-m-Chlorophenyl-piperazino)-ethyl 2-(8'-trifluoromethyl-4'-quinolyl-amino)-benzoate ($R_1 = CF_3$ in the 8-position;

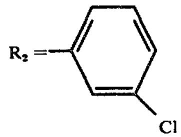

Code number: SL B 180).

A mixture of 10.76 g. (0.0289 mol) of allyl 2-(8'-trifluoromethyl-4'-quinolyl-amino)-benzoate, 7.21 g. (0.03 mol) of 2-(4'-m-chlorophenyl-piperazino)-ethanol, 0.07 g. of sodium and 150 ml. of anhydrous toluene is heated at the reflux temperature for 3 hours, following the procedure described in Example 17. The reaction mixture is filtered hot, and the toluene is evaporated from the filtrate. The residual paste-like product is triturated in petroleum ether and the precipitates which separates out is filtered off, washed, dried in vaco and recrystallised from ethanol. 13 g. (yield = 81%) of 2-(4'-m-chlorophenyl-piperazino)-ethyl 2-(8'-trifluoromethyl-4'-quinolyl-amino)-benzoate, m.p. 140° C., are obtained.

Analysis: $C_{29}H_{26}ClF_3N_4O_2$ (M.W. = 555.04) Calculated %: C 62.76, H 4.72, N 10.09, Cl 6.39 Found %: 62.68 4.75 9.96 6.46 6.30.

EXAMPLE 19

2-(4'-Phenyl-piperazino)-ethyl 2-(8'-trifluoromethyl-4'-quinolyl-amino)-benzoate.

($R_1 = CF_3$ in the 8-position; $R_2 = C_6H_5$ Code number: SL B 181).

Following the technique of Examle 17, a mixture of 10.76 g. (0.0289 mol) of allyl 2-(8'-trifluoromethyl-4'-quinolyl-amino)-benzoate, 7.426 g. (0.036 mol) of 2-(4'-phenyl-piperazino)-ethanol, 0.07 g. of sodium and 150 ml. of toluene is heated at the reflux temperature for approximately 3 hours. The reaction mixture is filtered and the toluene is evaporated from the filtrate. A solid residue is obtained which is washed with water, dried in vacuo and recrystallised from 2-propanol. 13 g. (yield = 86%) of 2-(4'-phenyl-piperazino)-ethyl 2-(8'-trifluoromethyl-4'-quinolyl-amino)-benzoate, m.p. 147° C., are thus obtained.

Analysis: $C_{29}H_{27}F_3N_4O_2$ (M.W. 520.559) Calculated %: C 66.91, H 5.61, N 10.76 Found %: 66.84 5.44 10.76 66.89 5.50.

EXAMPLE 20

2-(4'-m-Trifluoromethylthiophenyl-piperazino)-ethyl 2-(8'-trifluoromethyl-4'-quinolyl-amino)-benzoate ($R_1 = CF_3$ in the 8-position;

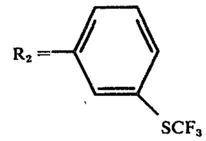

Code number: SLB 182).

Following the procedure of Example 17, a mixture of 10.76 g. (0.0289 mol) of allyl 2-(8-trifluoromethyl-4-quinolyl-amino)-benzoate, 10.11 g. (0.033 mol) of 2-(4-m-trifluoromethylphenyl-piperazino)-ethanol, 0.05 g. of sodium and 150 ml. of toluene is heated at the reflux temperature for 2 hours 30 minutes. The hot mixture is filtered, the toluene is evaporated from the filtrate and the gummy residue is triturated in petroleum ether. The precipitate which separates out is filtered off, dried in vacuo and recrystallised from 2-propanol. 15.6 g. (yield = 86%) of 2-(4'-m-trifluoromethylthiophenyl-piperazino)-ethyl 2-(8'-trifluoromethyl-4'-quinolyl-amino)-benzoate, m.p. 128° C., are obtained.

Analysis: $C_{30}H_{26}F_6N_4O_2S$ (M.W. = 610.621) Calculated %: C 58.06, H 4.22, N 9.03 Found %: 57.97 4.35 8.96.

EXAMPLE 21

2-(4'-m-Trifluoromethylphenyl-piperazino)-ethyl 2-(7'-trifluoromethyl-4'-quinolyl-amino)-benzoate

[(I), $R_1$ = —$CF_3$ in the 7-position,

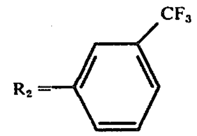

]

9.23 g. (0.0235 mol) of 2-(4'-m-trifluoromethylphenyl-piperazino)-ethyl 2-amino-benzoate, 7 g. (0.03 mol) of 4-chloro-7-trifluoromethyl-quinoline, 100 ml. of water and 20 ml. of 2N hydrochloric acid are introduced into a 250 ml. flask. This mixture is heated at the reflux temperature for two hours. The reaction mixture is allowed to cool, neutralised with a saturated solution of sodium bicarbonate, and extracted with methylene chloride. The organic phase is decanted, washed with water, dried over magnesium sulphate and filtered. The solvent is driven off from the filtrate and the residual solid is triturated in petroleum ether. The precipitate is filtered off and recrystallised from isopropyl alcohol.

10.95 g. (yield = π79.1%) of 2-(4'-m-trifluoromethyl-phenyl-piperazino)-ethyl 2-(7'-trifluoromethyl-4'-quinolyl-amino)-benzoate, m.p. 88°-90° C., are thus obtained.

EXAMPLE 22

2-(4'-m-Trifluoromethylphenyl-piperazino)-ethyl 2-(7'-chloro-4'-quinolyl-amino)-benzoate

[(I) $R_1$ = Cl in the 7-position,

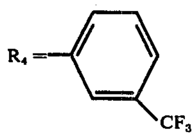

11.65 g. (0.025 mol) of 2-(4'-m-trifluoromethylphenyl-piperazino)-ethyl 2-amino-benzoate dihydrochloride are added to a suspension of 4.95 g. (0.025 mol) of 4,7-dichloro-quinoline in 100 ml. of water, and this mixture is heated at the reflux temperature for two hours. A further 4.95 g. (0.025 mol) of 4,7-dichloro-quinoline are added, and heating is continued until the reaction is complete. The mixture is cooled, and the precipitate which has formed is filtered off, washed with water, dried and recrystallised from isopropyl alcohol. 10.5 g. (yield = 66.8%) of 2-(4'-m-trifluoromethyl-phenyl-piperazino)-ethyl 2-(7'-chloro-4'-quinolyl-amino)-benzoate dihydrochloride are thus obtained.

The base is liberated by adding a saturated solution of sodium bicarbonate to a suspension of this dihydrochloride in water, and extraction with methylene chloride. The organic layer is isolated, washed several times with water, dried over magnesium sulphate and filtered. The solvent is evaporated from the filtrate and the solid residue is recrystallised from isopropyl alcohol. 6.75 g. (yield=72.6%) of 2-(4'-m-trifluoromethyl-phenyl-piperazino)-ethyl 2-(7'-chloro-4'-quinolyl-amino)-benzoate, m.p. 100°-102° C., are obtained.

EXAMPLE 23

2-(4'-m-Chlorophenyl-piperazino)-ethyl 2-(7'-chloro-4'-quinolyl-amino)-benzoate

[(I), $R_1$ = Cl in the 7-position,

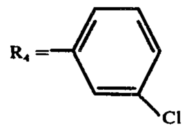

12.5 ml. of 2N hydrochloric acid are added to suspension of 6.44 g. (0.0325 mol) of 4,7-dichloro-quinoline and 9 g. (0.025 mol) of 2-(4'-m-chlorophenyl-piperazino)-ethyl anthranilate in 75 ml. of water. This mixture is heated at the reflux temperature for three hours, and then allowed to cool. The base is liberated by adding a saturated solution of sodium bicarbonate, and extracted with methylene chloride. The organic solution is decanted, washed several times with water, dried over sodium sulphate and filtered. The solvent is driven off from the filtrate and the residue is recrystallised from isopropyl alcohol. 9.95 g. (yield=76.4%) of 2-(4'-m-chlorophenyl-piperazino)-ethyl 2-(7'-chloro-4'-quinolyl-amino)-benzoate, m.p. 122° C., are collected.

EXAMPLE 24

2-(4'-m-Trifluoromethylthiophenyl-piperazino)-ethyl 2-(7'-trifluoromethyl-4'-quinolyl-amino)-benzoate

[(I), $R_1$ = —$CF_3$ in the 7-position,

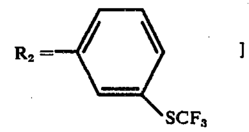

A suspension of 5.80 g. (0.025 mol) of 4-chloro-7-trifluoromethyl-quinoline and 9.96 g. (0.02 mol) of 2-(4'-m-trifluoromethylthiophenyl-piperazino)-ethyl 2-amino-benzoate dihydrochloride in 100 ml. of water is heated at the reflux temperature for four hours. The reaction mixture is cooled, and the precipitate is filtered off, washed with water, dried in vacuo in the presence of phosphorus pentoxide and recrystallised from isopropyl alcohol.

10.7 g. (yield = 77.4%) of 2-(4'-m-trifluoromethyl-thiophenyl-piperazino)-ethyl 2-(7'-trifluoromethyl-4'-quinolyl-amino)-benzoate dihydrochloride, m.p. 220° C., are obtained.

To obtain the base, a solution of sodium bicarbonate is added to the suspension of the dihydrochloride in water and the mixture is extracted with methylene chloride. The organic layer is washed with water, dried over sodium sulphate and filtered. The solvent is evaporated from the filtrate, and the base is obtained as an oil, which is purified by passage through a silica column (eluant,chloroform-acetone: 80-20). After evaporation of the solvents, 7.85 g. (yield = 82%) of 2-(4'-m-trifluoromethylthiophenyl-piperazino)-ethyl 2-(7'-trifluoromethyl-4'-quinolyl-amino) benzoate are obtained as a pale yellow oil.

EXAMPLE 25

2-(4'-Phenyl-piperazino)-ethyl 2-(8'-chloro-4'-quinolyl-amino)-benzoate

[(I), $R_1$ = Cl in the 8-position, $R_2 = C_6H_5$]

4.95 g. (0.025 mol) of 4,8-dichloro-quinoline, 6.5 g. (0.02 mol) of 2-(4'-phenyl-piperazino)-ethyl 2-amino-benzoate, 75 ml. of water and 10 ml. of 2N hydrochloric acid are heated at the reflux temperature for three hours. The base is liberated by adding a saturated solution of sodium bicarbonate to the reaction mixture. The precipitate obtained is filtered of, drained, washed several times with water, dried in vacuo in the presence of phosphorus pentoxide, and recrystallised from ethanol. 6.70 g. (yield = 68.7%) of 2-(4'-phenyl-piperazino)-ethyl 2-(8'-chloro-4'-quinolyl-amino)-benzoate, m.p. 164° C., are thus obtained.

EXAMPLE 26

2-(4'-Phenyl-piperazino)-ethyl 2-(7'-trifluoromethyl-4'-quinolyl-amino)-benzoate

[(I), $R_1 = CF_3$ in the 7-position, $R_2 = C_6H_5$].

23.1 g. (0.1 mol) of 4-chloro-7-trifluoromethyl-quinoline are added to a solution of 19.85 g. (0.05 mol) of 2-(4'-phenyl-piperazino)-ethyl 2-amino-benzoate dihydrochloride in 500 ml. of methanol. The pH of the mixture is adjusted to 2 by adding hydrocloric acid. The mixture is heated at the reflux temperature for eight hours. The mixture is filtered, the methanol is evaporated and the residue is taken up in a saturated solution of sodium bicarbonate to liberate the base which is extracted with methylene chloride. The organic solution is washed with water, dried over sodium sulphate and filtered. The solvent is evaporated from the filtrate, and the residue is recrystallised from isopropyl alcohol. 13.5 g. (yield = 52%) of 2-(4'-phenyl-piperazino)-ethyl 2-(7'-trifluoromethyl-4'-quinolyl-amino)-benzoate, m.p. 130° C., are obtained.

The compounds of the invention possess valuable pharmacological properties which make them useful for human and/or veterinary therapy.

Acute toxicity

Tests were carried out on mice of both sexes, of the Swiss strain, of average weight 20 g. (± 2g.). The 50% lethal doses were calculated according to Miller and Tainter (Proc. Soc. Exp. Biol. Med. 1944, 57, 261). The results are given in Table I.

TABLE I

| COMPOUND CODE NO. | ACUTE TOXICITY, MICE, ORAL ADMINISTRATION LD50* mg/kg |
|---|---|
| 72-165 | >2,000 |
| 72-242 | >3,000 |
| 72-244 | 1,200 |
| 72-248 | 1,900 |
| 72-391 | 2,500 |
| 73-017 | 1,500 |
| 73-018 | 4,000 |
| 73-030 | >4,000 |
| 73-031 | 3,000 |
| 73-033 | 4,000 |
| 73-045 | >4,000 |
| 73-046 | >2,000 |
| 73-047 | 3,000 |
| 73-048 | 4,000 |
| 73-051 | >4,000 |
| 73-069 | 2,200 |
| 73-070 | >4,000 |
| SLB 179 | >3,000 |
| SLB 180 | >3,000 |
| SLB 181 | 2,000 |
| SLB 182 | >3,000 |
| Amidopyrine | 850 |
| Phenylbutazone | 600 |
| Glafenine | 3,500 |

*LD50 = 50% lethal dose.

TABLE II

| COMPOUND | SIEGMUND TEST, MICE, ORAL ADMINISTRATION AD50* mg/kg |
|---|---|
| 72-165 | 50 |
| 72-242 | 25 |
| 72-244 | 10 |
| 72-248 | 20 |
| 72-391 | 20 |
| 73-017 | 4 |
| 73-018 | 6 |
| 73-030 | 100 |
| 73-031 | 100 |
| 73-033 | 5 |
| 73-045 | 8 |
| 73-046 | 13 |
| 73-047 | 16 |
| 73-048 | 6 |
| 73-051 | 16 |
| 73-069 | 50 |
| 73-070 | 16 |
| SLB 179 | 25 |
| SLB 180 | 12 |
| SLB 181 | 12 |
| SLB 182 | 5 |
| Amidopyrine | 50 |
| Phenylbutazone | 90 |
| Glafenine | 50 |

*AD50 = 50% active dose.

TABLE III

| COMPOUND | HEATED PLATE TEST, MICE, ORAL ADMINISTRATION MAD* mg/kg |
|---|---|
| 72-165 | >300 |
| 72-242 | 300 |
| 72-244 | 300 |
| 72-248 | 300 |
| 72-391 | 150 |
| 73-017 | 30 |
| 73-018 | 60 |
| 73-030 | 300 |
| 73-031 | 200 |
| 73-033 | 30 |
| 73-045 | 150 |
| 73-046 | 300 |
| 73-047 | 300 |
| 73-048 | >200 |
| 73-051 | >200 |
| SLB 179 | 100 |
| SLB 180 | 300 |
| SLB 181 | >300 |
| SLB 182 | 200 |
| Amidopyrine | 200 |
| Phenylbutazone | >200 |
| Glafenine | >600 |

*MAD = mean active dose.

Analgesic Activity

This activity was investigated by two different methods:

1. Effect against pain induced, in Swiss mice, by the intraperitoneal injection of phenylquinone, in accordance with the experimental procedure of Siegmund (Proc. Soc. Exp. Biol. Med., 1957, 95, 729), modified by Cheymol (C.R. Soc. Diol., 1963, 157, 521) and Brittain (Nature, London, 1963, 20, 895). The results are given in Table II below.

2. Tests using a plate heated by acetone vapours, carried out on Swiss mice, in accordance with the description by Woolfe (J. Pharmacol. Exp. Therap., 1944, 80, 300) with the modifications by Chen (Science 1951, 113, 631), Eddy (J. Pharmacol. Exp. Therap., 1953, 107, 385) and Boissier (Anesth. Analog., 1956, 13, 569).

Table III below gives the results obtained.

The results obtained in the Siegmund test, which demonstrates analgesic effects of the peripheral type, show that the compounds of the invention (72-242, 72-244, 72-248, 72-391, 73-017, 73-018, 73-033, 73-045, 73-046, 73-047, 73-048, 73-051, SLB 179, 180, 181 and 182) are generally much more active than the well-known analgesic agents used for comparison purposes (amidopyrine and glafenine).

In the heated plate test, which demonstrates analgesic effects of the central type, the compounds (72-391, 73-017, 73-018, 73-033, 73-045 and SLB 179) show an activity which is greater than that of amidopyrine. This greater activity is considerable in the case of the compounds 73-017, 73-018 and 73-033. In the case of the other compounds of the invention, the central component is, as in the case of glafenine, much less strong.

Anti-inflammatory activity

This activity was determined by the test involving oedema of the paw, induced in Sherman rats by the method of Winter and colleague (Proc. Soc. Exp. Biol. Med., 1962, 111, 544). The results are summarised in Table IV.

TABLE IV

| COMPOUND | CARRAGENINE-INDUCED OEDEMA TEST, RATS, ORAL ADMINISTRATION AD* mg/kg |
|---|---|
| 72-242 | 40 |
| 72-248 | 120 |
| 72-391 | 40 |
| 73-017 | 60 |
| 73-018 | 120 |
| 73-030 | 50 |
| 73-031 | 30 |
| 73-033 | 60 |
| 73-045 | 30 |
| 73-046 | 30 |
| 73-047 | 65 |
| 73-048 | 30 |
| 73-051 | 50 |
| 73-069 | 55 |
| 73-070 | >80 |
| SLB 179 | 120 |
| SLB 180 | >100 |
| SLB 181 | 45 |
| SLB 182 | 150 |
| Amidopyrine | 80 |
| Phenylbutazone | 30 |
| Glafenine | 30 |

*AD40 = 40% active dose.

These results show that the compounds of the invention have anti-inflammatory effects. These effects, which never exceed those of phenylbutazone administered at the same dosage, must be considered by taking into account the analgesic activity of the compounds of the invention which manifests itself at doses very much lower that the anti-inflammatory doses.

These experimental data show that the invention provides compounds having a very marked dissociation between analgesic and anti-inflammatory properties, in favour of the analgesic activity. This dissociation is of great value when it is considered that anti-inflammatory activity is frequently associated with mediocre or distinctly poor tolerance by the mucous membranes of the digestive tract.

Finally, and surprisingly, the toxicity of the majority of the compounds of the invention virtually does not increase at all with their activity, so that their therapeutic index is very much greater than that of glafenine.

The results show that the compounds of the invention can be used in human and veterinary therapy, and especially in the treatment of various algias, especially if they accompany inflammatory affections. The method of administration can be oral, rectal or parenteral, the active substances being used in conjunction with the usual excipients for these pharmaceutical forms. In the case of oral administration, for which tablets, dragees, capsules, gelatine-coated pills, potable solutions and the like, are used, the unit dose is 20 to 200 mg, the maximum daily dosage being 1 g. In the case of rectal administration, these figures are, respectively, from 50 to 400 mg. and 1 g., and in the case of parenteral administration, they are, respectively from 10 to 50 mg. and 0.5 g.

The invention accordingly includes within its scope pharmaceutical compositions comprising, in association with a compatible pharmaceutically acceptable diluent, a compound of formula I or a pharmaceutically tolerated acid addition salt thereof.

We claim:

1. An analgesic and anit-inflammatory composition comprising an analgesic or anti-inflammatory effective amount of a compound of the formula:

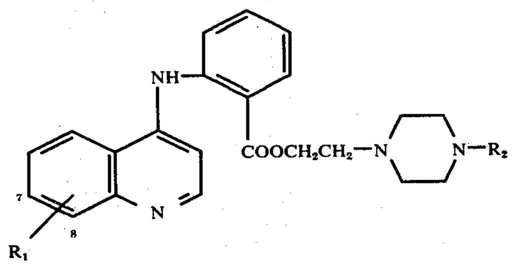

wherein $R_1$ is chlorine, trifluoromethyl or trifluoromethylthio; and $R_2$ is phenyl, chlorophenyl, methylphenyl, trifluoromethylphenyl, trifluoromethoxyphenyl, trifluoromethylthiophenyl, dimethylphenyl, chloromethylphenyl or ditrifluoromethylphenyl, $R_2$ being a substituted phenyl when $R_1$ is chlorine, or of a pharmaceutically acceptable acid addition salt thereof in combination with a pharmaceutically acceptable diluent.

2. The composition of claim 1 wherein $R_1$ is trifluoromethyl.

3. The composition of claim 1 wherein $R_1$ is 7-trifluoromethyl and $R_2$ is

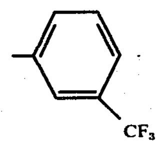

* * * * *

UNITED STATES PATENT AND TRADEMARK OFFICE
CERTIFICATE OF CORRECTION

PATENT NO. : 4,017,623

DATED : APRIL 12, 1977

INVENTOR(S) : Don Pierre René Lucien GIUDICELLI et al.

It is certified that error appears in the above-identified patent and that said Letters Patent are hereby corrected as shown below:

On the cover sheet Item (62) should read:

--[62] Division of Ser. No. 457,174, April 2, 1974, Pat. No. 3,935,229.--.

Signed and Sealed this

*Twenty-first* Day of *February 1978*

[SEAL]

*Attest:*

RUTH C. MASON
*Attesting Officer*

LUTRELLE F. PARKER
*Acting Commissioner of Patents and Trademarks*